United States Patent [19]

Warnant et al.

[11] 4,277,409
[45] Jul. 7, 1981

[54] PREPARATION OF 9α-FLUORO-16α-METHYL-21-ACETOXY-Δ$^{1,4}$-PREGNADIENE-11β-OL-3,20-DIONE

[75] Inventors: Julien Warnant, Neuilly-sur-Seine; Jean Jolly, Fontenay-sous-Bois, both of France

[73] Assignee: Roussel Uclaf, Paris, France

[21] Appl. No.: 94,772

[22] Filed: Nov. 16, 1979

Related U.S. Application Data

[63] Continuation of Ser. No. 886,122, Mar. 13, 1978, abandoned.

[51] Int. Cl.$^3$ .............................................. C07J 5/00
[52] U.S. Cl. ............................................. 260/397.45
[58] Field of Search ..................................... 260/397.45

[56] References Cited

U.S. PATENT DOCUMENTS

| | | | |
|---|---|---|---|
| 3,081,297 | 3/1963 | Wettstein et al. | 260/239.55 R |
| 3,251,866 | 5/1966 | Lincoln et al. | 260/397.45 |
| 3,312,692 | 4/1967 | Oliveto et al. | 260/239.5 |
| 3,375,261 | 3/1968 | Arth et al. | 260/397.45 |

*Primary Examiner*—Elbert L. Roberts
*Attorney, Agent, or Firm*—Hammond & Littell, Weissenberger and Muserlian

[57] ABSTRACT

An improved process for the preparation of pure 9α-fluoro-16α-methyl-21-acetoxy-Δ$^{1,4}$-pregnadiene-11β-ol-3,20-dione comprising reacting 9α-fluoro-21-acetoxy-Δ$^{1,4,16}$-pregnatriene-11β-ol-3,20-dione with a methyl magnesium halide in the presence of a catalytic amount of a cuprous halide effecting protonation of magnesian to form 9α-fluoro-16α-methyl-21-acetoxy-Δ$^{1,4}$-pregnadiene-11β-ol-3,20-dione, reacting the raw product with an acetylation agent to acetylate the partially deacetylated product and purifying the reacetylated product with an organic solvent, treating in solution with a peroxidation agent and then purifying again with an organic solvent.

13 Claims, No Drawings

PREPARATION OF 9α-FLUORO-16α-METHYL-21-ACETOXY-$\Delta^{1,4}$-PREGNADIENE-11β-OL-3,20-DIONE

PRIOR APPLICATION

This application is a continuation of copending, commonly assigned application Ser. No. 886,122 filed Mar. 13, 1978, now abandoned.

STATE OF THE ART

Reactions are known for introducing a 16α-methyl group into a steroid nucleus by reaction with methyl magnesium bromide in the presence of a catalytic amount of a cuprous halide. For example, French Pat. No. 2,244,530 describes the preparation of 16α-methyl-21-acetoxy-$\Delta^{1,4,9(11)}$-pregnatriene-3,20-dione starting from 21-acetoxy-$\Delta^{1,4,9(11),16}$-pregnatetraene-3,20-dione but the yields of the process are very mediocre.

In effect, the complex steroid molecules have numerous functional groups which are able to react with a reactive magnesian compound leading to numerous parasitic side reaction. Besides the methylation reaction in the 16α-position of 9α-fluoro-21-acetoxy-$\Delta^{1,4,16}$-pregnatriene-11β-ol-3,20-dione to obtain 9α-fluoro-16α-methyl-21-acetoxy-$\Delta^{1,4}$-pregnadiene-11β-ol-3,20-dione, there are other reactions that may occur. In effect, the said starting triene compound has many functions capable of reacting with an active magnesian such as the 3-keto group, double bonds in the 1 and 4 positions, the 20-keto group and the 21-acetoxy group as well as the double bond in the 16-position. This means a priori that there may be the formation of a great number of side reactions leading to a very low yield of the desired product.

Studies have shown that in general when the said reaction is effected under non-special operating conditions, diverse side reactions effectively take place. There has been observed the formation of 3-methylene-9α-fluoro-16α-methyl-21-acetoxy-$\Delta^{1,4}$-pregnadiene-11β-ol-20-one by attack of the 3-keto group, of 9α-fluoro-16α-methyl-$\Delta^{1,4}$-pregnadiene-11β,21-diol-3,20-dione by saponification of the 21-acetoxy group as well as a low percentage of 1α-methyl-9α-fluoro-16α-methyl-21-acetoxy-$\Delta^{1}$-pregnene-11β-ol-3,20-dione by attack of the 1,2-double bond and of 9α-fluoro-$\Delta^{1,4,16}$-pregnatriene-11β-ol-3,20-dione by reduction of the 21-hydroxy group. There can also be mentioned the French Pat. No. 2 318 647 which described alkylation reaction in the 16α-position of steroid compounds different from the compound of the present application and in which the final aim of the synthesis is different.

OBJECTS OF THE INVENTION

It is an object of the invention to provide a process for the 16α-methylation of 9α-fluoro-21-acetoxy-$\Delta^{1,4,16}$-pregnatriene-11β-ol-3,20-dione with optimum yields.

This and other objects and advantages of the invention will become obvious from the following detailed description.

THE INVENTION

The novel process of the invention for the preparation of pure 9α-fluoro-16α-methyl-21-acetoxy-$\Delta^{1,4}$-pregnadiene-11β-ol-3,20-dione comprises reacting 9α-fluoro-21-acetoxy-$\Delta^{1,4,16}$-pregnatriene-11β-ol-3,20-dione with a methyl magnesium halide in the presence of a catalytic amount of a cuprous halide, effecting protonation of magnesian to form 9α-fluoro-16α-methyl-21-acetoxy-$\Delta^{1,4}$-pregnadiene-11β-ol-3,20-dione, reacting the raw product with an acetylation agent to acetylate the partially deacetylated product and purifying the reacetylated product with an organic solvent, treating in solution with a peroxidation agent and then purifying again with an organic solvent.

Preferably, the methyl magnesium halide is methyl magnesium bromide and the cuprous halide is cuprous chloride. The 9α-fluoro-21-acetoxy-$\Delta^{1,4,16}$-pregnatriene-11β-ol-3,20-dione is reacted with 1.8 to 3.2 mols of methyl magnesium bromide per mole of steroid in the presence of a catalytic quantity of cuprous chloride at a temperature of $-20°$ to $-60°$ C., the reaction mixture is treated at a low temperature with methanol and then with an aqueous solution of a mineral salt, the raw product is acetylated with acetic anhydride, the raw reacetylated product is purified by empasting or crystallization in an organic solvent, treated in solution with perphthalic acid and purified by empasting or crystallization in an organic solvent to obtain pure 9α-fluoro-16α-methyl-21-acetoxy-$\Delta^{1,4}$-pregnadiene-11β-ol-3,20-dione.

Effecting the condensation of the magnesium halide and the steroid at temperatures different from those of the invention results in clearly inferior yields. The preferred reaction temperature of the invention is $-45°\pm3°$ C. since at this temperature, the starting steroid is completely reacted and the secondary reactions were kept to a minimum.

The preferred amount of methyl magnesium bromide is 1.8 to 3.2 moles per mole of starting steroid with the theoretical amount of methyl magnesium bromide being 2 moles per mole of steroid because of the presence of the 20-keto group. The most advantageous amount of methyl magnesium bromide used is about 2.5 moles per mole of starting steroid since the reaction with the starting steroid is practically total and secondary reactions are limited at this ratio.

The cuprous halide to be used may be the bromide, chloride or iodide but the preferred one is cuprous chloride. The amount of cuprous chloride used in the reaction is perferably 1 to 5% by weight of the starting steroid with the optimum amount being 2% by weight based on the starting steroid.

The protonation of the magnesium derivative with the carbon in the 20-position when effected under classical conditions such as by pouring the reaction mixture into an aqueous ammonium chloride solution results in irregular yields. Studies have shown that the protonation of the magnesium derivative is advantageously effected by addition of methanol at a temperature of $-35°$ C.$\pm 10°$ C. Under these conditions, the yields are constant and higher than those when class protonation reactions are used.

The acetylation of the raw product may be effected by reaction with classical acetylation reactants and the preferred reactant is acetic anhydride in the presence of pyridine. This acetylation is essential since the reaction with magnesium effects a partial desacetylation of the 21-hydroxyl.

After reacetylation of the raw product, a first purification of the product is effected by empasting or crystallization in a solvent preferably selected from the group consisting of dichloroethane, methylene chloride, chlorobenzene, alkanols of 1 to 4 carbon atoms, ethyl acetate, benzene and toluene. The first purification is effected by empasting in dichloroethane.

The perphthalic acid treatment which takes place after the first purification in a solvent is preferably effected by dissolving the purified, reacetylated product in chloroform and then adding an ether solution of perphthalic acid although other solvents may be used for the reaction.

The treatment with perphthalic acid results in selective epoxidation of the 3-methylene of 3-methylene-9α-fluoro-16α-methyl-21-acetoxy-$\Delta^{1,4}$-pregnadiene-11β-ol-20-one impurity formed in small amounts under the special operating conditions of the process of the invention. This impurity is very difficult to remove by empasting or crystallization from a solvent but the epoxidized form resulting from the perphthalic acid treatment is easily removed with a conveniently selected solvent.

After the perphthalic acid treatment, the product is efficacily purified by empasting or crystallization in an alkanol of 1 to 4 carbon atoms. Preferred is crystallization from methanol.

The original character of the process of the invention consists in the selection of operating conditions for the reaction of magnesian with the double bond in the 16,17-position being predominant with the side reactions being held to a minimum. Moreover, the use of a starting steroid molecule possessing several reactive functions which don't permit to completely supress certain undesirable side reactions, the process of the invention has also resolved with efficiency the problem of removing the formed impurities by desacetylation in the 21-position by the simple expedient of reacetylation with acetic anhydride and the 3-methylene compound by transformation into the corresponding epoxidized compound by treatment of perphthalic acid is easily removed by purification with a convenient solvent. Finally, contrary to what one skilled in the art would expect, the process of the invention despite the foreseeable secondary reactions permits to obtain in satisfactory yields 9α-fluoro. 16α-methyl-21-acetoxy-$\Delta^{1,4}$-pregnadiene-11β-ol-3,20-dione which is a useful intermediate for the preparation of 9α-fluoro-16α-methyl-$\Delta^{1,4}$-pregnadiene-11β-21α-diol-3,20-dione which is extensively used in human theraphy.

In the following example there are described several preferred embodiments to illustrate the invention. However, it is to be understood that the invention is not intended to be limited to the specific embodiments.

EXAMPLE

9α-fluoro-16α-methyl-21-acetoxy-$\Delta^{1,4}$-pregnadiene-11β-ol-3,20-dione

STEP A: Condensation 70 g of methyl bromide were added under nitrogen at 10° C. with stirring over one hour to a mixture of 16 g of magnesium in 200 ml of ether and after stirring for 30 minutes, the mixture was progressively heated while distilling ether. The temperature was increased to 40° C. and 500 ml of tetrahydrofuran were added to the mixture over 30 minutes. The temperature was raised to 60° C. and the rest of the ether was distilled to obtain a slightly turbid solution titrating about one mole per liter of methyl magnesium bromide.

Sufficient tetrahydrofuran was added to 470 ml of the said solution to adjust the titer of the solution to 0.5 mole/liter or 470 ml of tetrahydrofuran and 1.5 g of cuprous chloride were added thereto. The mixture was stirred for 15 minutes at 20° C. and was cooled to −45° C. A solution of 75 g of 9α-fluoro-21-acetoxy-$\Delta^{1,4,16}$-pregnatriene-11β-ol-3,20-dione in 675 ml of tetrahydrofuran was added to the mixture at −45° C. over one hour and the temperature was progressively increased over 30 minutes to −27° C. The mixture was stirred at −27° C. for 4 hours and was then cooled to −35° C. and 150 ml of methanol were added over 15 minutes. The mixture was stirred at −35° C. for 15 minutes and then rapidly poured at 5° C. with stirring into a solution of 450 g of ammonium chloride in 1500 ml of water. The mixture was stirred at 5° C. for 15 minutes and the temperature was allowed to rise to 20° C. The organic phase was decanted and the aqueous phase was extracted with tetrahydrofuran. The combined organic phases were washed with an aqueous 30% ammonium chloride solution and the wash waters were extracted with tetrahydrofuran. The organic extracts were washed with an aqueous 30% ammonium chloride solution and the combined organic phase were dried over magnesium sulfate. Activated carbon was added to the mixture which was stirred, filtered and concentrated to a volume of 150 ml.

STEP B: Reacetylation 300 ml of pyridine were added to 150 ml of the reaction mixture of Step A and the mixture was concentrated to 150 ml to remove residual water. The mixture was cooled to 20° C. and after the addition of 75 ml of acetic anhydride thereto, the mixture was stirred for 4 hours at 20° C. under a nitrogen atmosphere and was then poured into a mixture of water, ice and 187.5 ml of aqueous 22° Be hydrochloric acid solution. The mixture was stirred and vacuum filtered and the recovered product was washed with water and dried to obtain 75.1 g of raw product. The latter was empasted at reflux with 3 volumes of dichloroethane for 15 minutes, was stirred for 3 hours at 0° C., vacuum filtered and dried to obtain 44.6 g of raw 9α-fluoro-16α-methyl-21-acetoxy-$\Delta^{1,4}$-pregnadiene-11β-ol-3,20-dione melting at 245° C. and having a specific rotation of $[\alpha]_D^{20} = 127°$ (c=1% in dimethylformamide).

STEP C: Purification

The raw product of Step B was dissolved in 1560 ml of chloroform and 14.9 ml of an ether solution of perphthalic acid titrating 0.13 g/ml were added thereto. The mixture was stirred at 20° C. for 17 hours and water containing 10% ammonium hydroxide was added thereto. The mixture was stirred and decanted and the organic phase was washed with water containing 10% ammonium hydroxide and the wash waters were extracted with chloroform. The chloroform extracts were washed with water and the combined organic phases were dried over magnesium sulfate, stirred with activated carbon and filtered. The filtrate was concentrated to a volume of 225 ml and 225 ml of methanol were added thereto. The mixture was refluxed until dissolution occured and 150 ml of methanol were added thereto. The mixture was evaporated to dryness and the methanol treatment was repeated once to completely remove chloroform. The temperature returned to 20° C. and the mixture was stirred for one hour and was vacuum filtered. The recovered product was washed with methanol and dried to obtain 40.9 g of 9α-fluoro-16α-methyl-21-acetoxy-$\Delta^{1,4}$-pregnadiene-11β-ol-3,20-dione melting at 248° C. and having a specific rotation of $[\alpha]_D^{20} = 128°$ (c=1% in dimethylformamide).

Various modifications of the process of the invention may be made without departing from the spirit or scope thereof and it is to be understood that the invention is intended to be limited only as defined in the appended claims.

We claim:

1. In the process for the preparation of pure 9α-fluoro-16α-methyl-21-acetoxy-$\Delta^{1,4}$-pregnadiene-11β-ol-3,20-dione comprising reacting 9α-fluoro-21-acetoxy-$\Delta^{1,4,16}$-pregnatriene-11β-ol-3,20-dione with a methyl magnesium halide in the presence of a catalytic amount of a cuprous halide effecting protonation of magnesium to form 9α-fluoro-16α-methyl-21-acetoxy-$\Delta^{1,4}$-pregnadiene-11β-ol-3,20-dione, treating the reaction mixture with methanol, reacting the raw product with an acetylation agent to acetylate the partially deacetylated product and purifying the reacetylated product with an organic solvent, the improvement comprising treating the solution with a peroxidation agent to epoxidize the impurity, and then removing the epoxidized impurity with an organic solvent.

2. The process of claim 1 wherein the methyl magnesium halide is methyl magnesium bromide and the cuprous halide is cuprous chloride.

3. The process of claim 1 wherein 9α-fluoro-21-acetoxy-$\Delta^{1,4,16}$-pregnatriene-11β-ol-3,20-dione is reacted with 1.8 to 3.2 moles of methyl magnesium bromide per mole of steroid in the presence of a catalytic quantity of cuprous chloride at a temperature of $-20°$ to $-60°$ C., the reaction mixture is treated at a low temperature with methanol and then with an aqueous solution of a mineral salt, the raw product is acetylated with acetic anhydride, the raw reacetylated product is purified by empasting or crystallization in an organic solvent, treated in solution with perphthalic acid and purified by empasting or crystallization in an organic solvent to obtain pure 9α-fluoro-16α-methyl-21-acetoxy-$\Delta^{1,4}$-pregnadiene-11β-ol-3,20-dione.

4. The process of claim 1 wherein the reaction with methyl magnesium halide is effected at $-45°\pm3°$ C.

5. The process of claim 1 wherein the reaction is effected with about 2.5 moles of methyl magnesium bromide per mole of starting steroid.

6. The process of claim 1 wherein the amount of cuprous chloride is about 1 to 5% by weight based on the starting steroid.

7. The process of claim 1 wherein the said amount is 2% of cuprous chloride.

8. The process of claim 3 wherein the reaction with methanol is effected at $-35°$ C.$\pm10°$ C.

9. The process of claim 1 wherein the purification of reacetylated product is purified by empasting or crystallization from a solvent selected from the group consisting of dichloroethane, methylene chloride, chlorobenzene, alkanols of 1 to 4 carbon atoms, ethyl acetate, benzene and toluene.

10. The process of claim 9 wherein the purification is effected by empasting in dichloroethane.

11. The process of claim 3 wherein the perphthalic acid treatment is effected by dissolution of the purified and reacetylated product in chloroform and an ether solution of perphthalic acid is added thereto.

12. The process of claim 3 wherein the expoxidized product is removed by empasting or crystallizing from alkanol of 1 to 4 carbon atoms.

13. The process of claim 12 wherein the removal is effected by crystallization from methanol.

* * * * *

UNITED STATES PATENT AND TRADEMARK OFFICE
CERTIFICATE OF CORRECTION

PATENT NO. : 4,277,409
DATED : July 7, 1981
INVENTOR(S) : JULIEN WARNANT and JEAN JOLLY It is certified that error appears in the above—identified patent and that said Letters Patent is hereby corrected as shown below:

On the title page, Insert:

-- [30] Foreign Application Priority Data

March 18, 1977 [FR]    France 77 08170 --

Column 2; line 54: "class" should read -- classic --.

Signed and Sealed this

Sixteenth Day of March 1982

|SEAL|

*Attest:*

*Attesting Officer*

GERALD J. MOSSINGHOFF

*Commissioner of Patents and Trademarks*